United States Patent [19]

Harsh et al.

[11] Patent Number: 4,904,244
[45] Date of Patent: Feb. 27, 1990

[54] APPARATUS FOR SAFELY REMOVING NEEDLES FROM HYPODERMIC SYRINGES

[76] Inventors: Don J. Harsh, 5670 S. 920 East; Linda R. Hills, 6298 S. Lorreen Dr., both of Salt Lake City, Utah 84121; Kennalyn Howard, 3706 Market St., West Valley City, Utah 84119

[21] Appl. No.: 158,767

[22] Filed: Feb. 22, 1988

[51] Int. Cl.⁴ .............................................. A61M 5/00
[52] U.S. Cl. .................................... 604/187; 604/241; 604/110
[58] Field of Search .................... 604/187, 240–243, 604/110

[56] References Cited

U.S. PATENT DOCUMENTS

| | | | |
|---|---|---|---|
| 4,139,009 | 2/1979 | Alvarez. | |
| 4,237,882 | 12/1980 | Wickham. | |
| 4,425,120 | 1/1984 | Sampson et al. | 604/198 |
| 4,490,142 | 12/1984 | Silvern | 604/241 |
| 4,592,744 | 6/1986 | Jagger et al. | 604/192 |
| 4,596,562 | 6/1986 | Vernon | 604/192 |
| 4,631,057 | 12/1986 | Mitchell | 604/198 |
| 4,655,751 | 4/1987 | Harbaugh | 604/198 |
| 4,664,653 | 5/1987 | Sagstetter et al. | 604/197 |
| 4,681,567 | 7/1987 | Masters et al. | 604/198 |
| 4,693,708 | 9/1987 | Wanderer et al. | 604/198 |

FOREIGN PATENT DOCUMENTS 883053 7/1953 Fed. Rep. of Germany ...... 604/187

OTHER PUBLICATIONS

"University of Utah, Occupational Health Memorandum" dated Jan. 11, 1988.

Primary Examiner—John D. Yasko
Attorney, Agent, or Firm—Workman, Nydegger & Jensen

[57] ABSTRACT

An apparatus for removing needles from a hypodermic syringe is provided. The syringe is of the type having a barrel and a needle socket. The present invention teaches placing a collar apparatus between the base of the needle and the end of the syringe barrel in the region of the needle socket. The present invention also provides means for causing the collar to move generally away from the syringe barrel such that the collar causes the needle to be disengaged from the needle socket.

Several embodiments of the present invention are disclosed. For example, in one embodiment one or more curved elongated arms are attached at their distal end to the collar. As their proximal end, they are securely attached to the syringe. Thus, when the arms are pressed inwardly the collar is forced to move forward disengaging the syringe from the syringe socket. Other alternative embodiments are also disclosed including means for removing Luer lock needles from syringes, and a sheath or rigid generally cylindrical tube placed over the syringe barrel. In both cases, the sheath and tube are moved forward in such a manner as to cause the collar to disengage the needle from the syringe barrel.

16 Claims, 4 Drawing Sheets

APPARATUS FOR SAFELY REMOVING NEEDLES FROM HYPODERMIC SYRINGES

BACKGROUND OF THE INVENTION

1. Field of the Invention

The present invention is related to an apparatus for allowing the safe removal of used needles from hypodermic syringes. More particularly, the present invention relates to an apparatus for pushing needles off a syringe without the necessity of grasping or recapping the used needles.

2. Background of the Invention

A very serious practical problem in medical treatment is the removal of needles from hypodermic syringes once those needles have been used. Often syringes and needles are disposed of separately. As a result, it is necessary, after each injection or other use of a hypodermic syringe, for the medical personnel to attempt to remove the needle from the syringe for disposal. The removal of a needle from a syringe, however, is a potentially dangerous procedure.

Installing a new needle on the end of a syringe in preparation for use is generally quite safe and easy in that needles are packaged in solid plastic sheaths or in some other similar manner that covers the needle point until the needle is securely installed on the syringe. Thus, the plastic sheath or the like can be safely grasped and the needle can be securely fit onto the end of the syringe, either by friction or by twisting the needle onto a "Luer" connection. The sheath is designed for easy removal once the needle is secured to the syringe body. Thus, installation of the needle takes place without exposing the user to the needle point.

Removal of used needles from the ends of syringes is a much more difficult and potentially dangerous process. Initially, it must be recognized that the needle is not capped at the time of removal. Some users inevitably attempt to recap the needles before removal. This procedure is not the generally preferred method of disposal and can result in accidental penetration of the needle into the hands and arms of the medical personnel in the event that the user is unable to immediately fit the cap over the needle. Such needle penetrations are often referred to as "needle sticks." Thus, medical personnel are faced with the problem of undoing a friction attachment, or with twisting and pulling a needle, in order to eject it from the end of the syringe body. This obviously presents a substantial danger of injury due to penetration by the exposed needle point.

In many hospitals and other medical facilities, needles sticks are far and away the most frequent cause of injury to medical personnel. For example, in one major university hospital it was found that there were 199 reported incidents of "needle stick" in a single year. In the same hospital, it was not unusual to find 20-30 reported needle stick accidents in any particular month.

In a survey of the causes of needle sticks it was found that the greatest instances of such accidents occurred during disposal of the needles or in attempted recapping of the needle following use. Thus, as would be expected penetration by used needles, rather than by fresh needles, is the major source of injury.

The potential for serious and painful injury following penetration by used hypodermic needles is obvious. Uncontrolled penetration of an individual by any extremely sharp object can result in serious physical injury. Indeed, needle sticks can cause injury similar to penetration by a small knife or other sharp instrument.

Apart from the potential for serious physical injury, an additional serious problem with needle sticks is the transmission of disease. In that needles are often used to give injections to seriously ill individuals, it is not surprising to find the transmission of communicable diseases by way of needle stick. This has become a particularly serious problem in recent years due to the spread of acquired immune deficiency syndrome (AIDS) and other diseases transmitted by exposure to blood or body fluids. Medical and hospital personnel are taking ever increasing precautions to minimize the transmission of diseases such as AIDS in the hospital setting. These precautions include increased use of masks and gloves when treating individuals with certain ailments. It will be readily appreciated that a single needle stick, however, can quickly defeat all of the precautions taken in other areas.

While AIDS is of major concern, other communicable and infectious diseases can also easily be transmitted by way of needle stick. Any type of infectious disease could be passed along to the medical personnel by penetration with a used needle. Diseases ranging from hepatitis to the common cold are of concern.

While various attempts have been made to address the problem of penetration by used needles, no widely accepted solution has been developed. For example, devices which basically include the use of an outer sheath on the syringe barrel have been developed. When the needle is not in use, the sheath slides forward until it covers the tip of the exposed needle. Many different configurations of this type of device are known in the art.

It will be appreciated, however, that constructing a needle sheath does not deal directly with the problem of removal of used needles from syringe bodies. Sheaths of the type mentioned above simply allow medical personnel to cover the needle while it is still attached to the hypodermic syringe. Thus, these types of sheaths do not in actuality deal with the problem of needle removal. These devices simply help protect the needle point between uses.

Other types of sheaths have also been developed. For example, collapsible sheaths which are permanently mounted to the exterior of the needle have been developed. When the needle is used during injection, the sheath collapses or folds toward the syringe barrel. When the injection is completed, the sheath again expands covering the needle. Again, however, these mechanisms simply provide a means for covering an exposed needle while the needle is not in use.

While some of the sheaths describe above may be fit with a feature which aids in the removal of the needle, this type of device is not very useful in everyday practice. The sheaths described above are cumbersome, expensive, and are not easily retrofit onto conventional commonly used syringes. As a result, these devices do not solve the problem of needle removal in common practice. Needle sheaths of the type described are more adaptable for use in situations requiring specialized equipment and repeated use of the needle.

In order to solve the problem of needle removal in everyday practice it is necessary to develop a device which allows needles to be removed from conventional, widely used syringe types. In addition, since cost and convenience are both important considerations, it would be desirable to provide an inexpensive and disposable mechanism for removing such needles. Such a mechanism would necessarily be compatible with inexpensive, disposable syringes and needles. A mechanism which requires reuse and sterilization is cumbersome and labor intensive in its use and, as a result, is not particularly practical in everyday use.

Accordingly, it would be a significant advancement in the art to provide an apparatus which aided medical personnel in removing used needles from hypodermic syringes. It would be a further advancement in the art if such a device could be used in connection with conventional and widely accepted syringe types. In particular, it would be an advancement in the art if such a device could be retrofit onto conventional existing syringes. It would also be an advancement in the art to provide a simple and inexpensive device for removal of used needles from syringe bodies. This would allow the device to be disposed of along with the used syringe and needle once use was completed.

Such methods and apparatus are disclosed and claimed herein.

BRIEF SUMMARY AND OBJECTS OF THE INVENTION

The present invention is related to methods and apparatus for removing used needles from the ends of hypodermic syringes. As discussed above, the removal of used needles from syringes is a difficult and often dangerous procedure. The present invention overcomes the problems of the prior art and provides a simple, inexpensive, and easily used device for removing such used needles.

The present invention can take the form of several different embodiments. The basic concept, however, is that the device aids in pushing a needle off the needle socket on the end of the syringe barrel. Alternatively, in the case of screw on needles, such as Luer lock needles, the present invention provides means for twisting the needle away from the needle socket without grasping the needle.

The removal procedure is accomplished entirely without exposing medical personnel to the sharp end of the needle. The needle is either covered by the device during removal, or the removal procedure takes place with the medical personnel grasping the device in the vicinity of the syringe barrel, rather than near the needle point.

The invention provides a collar between the base of the needle and the syringe barrel. The collar may take on any desired configuration. One common type of configuration is a collar in the shape of a disk. The disk will normally have a hole in its center such that the needle socket can protrude through the collar. Thus, the collar does not interfere with the attachment of the needle to the needle socket.

The present invention also provides means for forcing the collar forward in the direction of the needle when it is desired to remove the needle. In the case of conventional friction fit needles, the collar moves directly forward. In the case of needles that are screwed onto the needle socket, the collar moves forward by way of a twisting motion. In either event, the present invention provides means for forcing the collar forward a sufficient distance to disengage the needle from the needle socket, which is generally formed as part of the syringe barrel.

In one preferred configuration, the means for moving the collar forward comprises one or more curved arms. The curved arms are attached at their distal ends to the collar. At their proximal ends, the arms are secured to the syringe barrel. When the arms are attached to both the collar and the syringe barrel, the arms protrude outwardly from the syringe barrel.

Employing this configuration of the device, a user grasps the syringe barrel. By placing pressure, such as with the thumb and forefinger, on the outwardly protruding arms and pushing them inwardly toward the syringe barrel, the collar is forced forward in the direction of the needle. The arms are configured such that the collar moves a sufficient distance to disengage the needle from the syringe barrel. As a result, the pressing action by the user easily and safely causes the needle to be removed from the end of the syringe.

It will be appreciated that the outwardly extending arms may be anchored to the syringe barrel in a number of different ways. For example, a ring structure may be positioned on the outside of the barrel, with the arms securely attached to the ring. Alternatively, pockets may be molded into the side of the syringe barrel and the outwardly extending arms positioned within the pockets when it is desired to use the device.

In any event, this embodiment of the present invention solves the problems encountered in the art. The outwardly extending arm or arms, the collar, and the anchor apparatus can be easily molded of plastic in a very inexpensive manner. As a result, conventional syringes are easily and inexpensively retrofit with the device. Alternatively, conventional syringes can be constructed with the outwardly extending arm apparatus already molded in place.

Other alternative embodiments of the device also fall within the scope of the present invention. For example, the collar can be attached to a cylindrical, rigid, outward covering of the syringe body. Using this embodiment, the outer covering is pressed forward, sliding along the outside of the syringe body. This causes the collar to move forward, removing the needle from the needle socket in the manner described above.

Alternatively, a flexible sheath may be provided which covers a portion of the syringe barrel prior to use. The sheath terminates at its forward end with the collar apparatus described above. Again, the collar is placed beneath the base of the needle in the area of the syringe socket. When it is desired to remove the needle, the sheath is grasped in the area of the syringe barrel and pulled forward over the top of the needle. The sheath is moved forward continuously until the collar engages the base of the needle forcing the needle from the needle socket. The needle is then enclosed by the sheath, and the sheath and needle can be disposed of together.

In the case of a Luer-type screw connection, the device may take the form of a wing nut or similar type of apparatus which engages the collar, which in turn engages the base of the needle. When the wing nut is twisted, the threaded needle disengages from the threaded needle socket and moves away from the syringe.

Accordingly, it is a principal object of the present invention to provide methods and apparatus for safely removing used needles from the ends of hypodermic syringes.

It is a related object of the present invention to provide methods and apparatus which allow medical personnel to remove needles from syringes without the necessity of grasping the needle or performing any manual function in the vicinity of the needle point.

It is also an object of the present invention to provide a collar device which resides between the base of the needle and the syringe body.

It is a further object of the present invention to provide means for moving the collar device forward sufficiently to disengage the needle from the needle socket.

It is an additional object of the present invention to provide such methods and apparatus which allow for easy retrofit onto conventional syringes and which are simple and economical to manufacture and use.

These and other objects of the present invention will become apparent upon reading the following detailed description and appended claims and upon reference to the accompanying drawings.

DETAILED DESCRIPTION OF THE PREFERRED EMBODIMENTS

Figure 1:
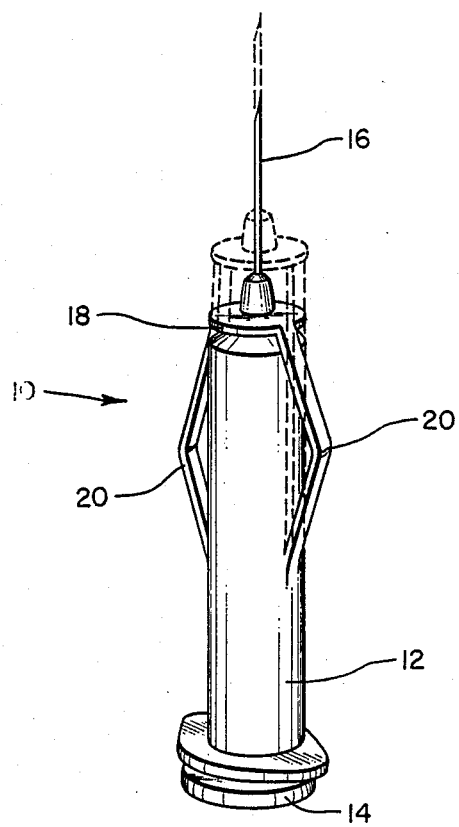
FIG. 1 is a side perspective view of one embodiment of the present invention.

The present invention can be best understood by reference to the drawings, wherein like parts are designated with like numerals throughout. Referring more particularly to FIG. 1, a first embodiment within the scope of the present invention is illustrated. The present invention is related to methods and apparatus for removing needles from the ends of hypodermic syringes without the necessity of touching the needle.

The invention is designated generally with the numeral 10 in FIG. 1. A standard syringe barrel 12 is also illustrated. Reciprocating within the interior of the syringe barrel 12 is a conventional syringe plunger 14.

Also illustrated in FIG. 1 is a conventional hypodermic syringe needle 16 which rests on a needle socket. The view of the needle socket in FIG. 1 is obscured by the needle which is secured in place over the needle socket.

The present invention comprises an apparatus for removing the hypodermic needle 16 from the syringe needle socket. In particular, the present invention comprises a collar 18. Collar 18, when the device is in operation, rests between the distal end of the syringe and beneath the base of the needle 16. The collar 18 encompasses the needle socket disposed on the distal end of the syringe barrel 12.

Extending outwardly and downwardly from the collar 18 are a pair of arms 20. As shown in FIG. 1, the arms are attached to the collar at their distal ends and are molded in attachment to the syringe barrel at their proximal ends. When the device 10 is in position, the arms extend outwardly from the syringe barrel in the manner illustrated in FIG. 1.

The method of operation of the device illustrated in FIG. 1 can be readily appreciated from the phantom lines shown in FIG. 1. Initially, the user of the device presses inwardly on the arms 20. The movement of the arms 20 toward the syringe barrel will cause the distal ends of the arms to move forward, causing in turn the collar 18 to move forward. This movement of the collar lifts the needle from the end of the needle socket. When the arms 20 are pressed firmly against the barrel of the syringe, the collar 18 is moved sufficiently forward to totally disengage the needle 16 from the needle socket. Thus, it is possible to remove the needle from the end of the hypodermic syringe without the necessity of the touching the needle.

Figure 2:
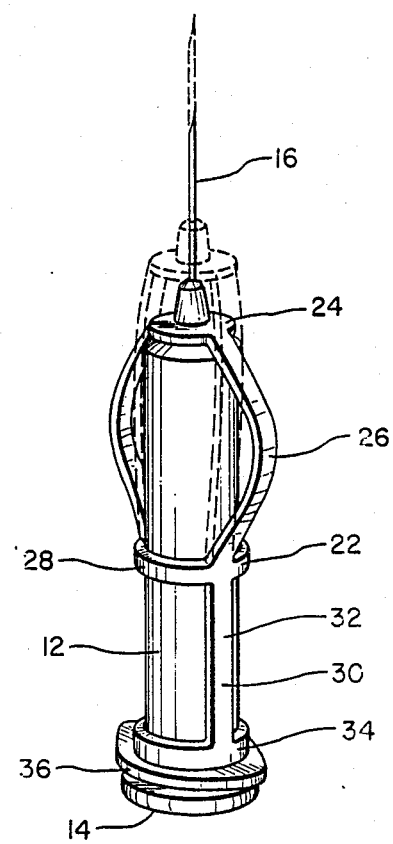
FIG. 2 is a side perspective view of an alternative embodiment of the present invention with phantom lines indicating the manner in which the invention is installed on the outside of a syringe barrel.

FIG. 2 illustrates a slightly different embodiment of the present invention. As with FIG. 1, a hypodermic syringe barrel 12 is illustrated, as are the plunger 14 and the hypodermic needle 16. In the embodiment of the device illustrated in FIG. 2, the device is retrofit onto the syringe barrel 12 rather than molded to the syringe barrel 12. That is, the device 22 simply slides over the outside of syringe barrel 12. Once in place the needle 16 can be attached to the needle socket on the end of the syringe barrel.

As with the embodiment of the device illustrated in FIG. 1, this embodiment includes a collar 24 and at least one arm 26 attached at its distal end to the collar. As illustrated in FIG. 2, the device comprises two arms; however, it will be appreciated that any number of arms may be used as needed and desired.

The arms are attached at their proximal end to a ring 28. The ring 28 is in turn attached to a base structure 30. The base structure as illustrated essentially comprises one or more solid posts 32 which are in turn attached to a base ring 34. The base ring 34 rests against the syringe barrel flange 36 which is molded as a part of the syringe barrel 12. Thus, the device 22 is securely positioned on the exterior of the syringe barrel 12. The arms 26 are securely anchored at their proximal ends such that pressing inwardly on the arms causes the distal end of the arms to move forward. It will also be appreciated that it is easy to retrofit a standard syringe barrel 12 with the device in that this entails simply sliding the device over the outside of the syringe barrel.

The method of operation of the device as illustrated in FIG. 2 can be readily appreciated by reference to the phantom lines in FIG. 2. In a manner similar to that used in operating the device as illustrated in FIG. 1, the user simply presses on the arms 26 such that they move inwardly toward the syringe barrel 12. This motion causes the collar 24 to move forward a sufficient distance to disengage the needle 16 from the syringe socket. Thus, the needle 16 is again removed from the syringe barrel without the necessity of grasping the needle 16.

Figure 3:
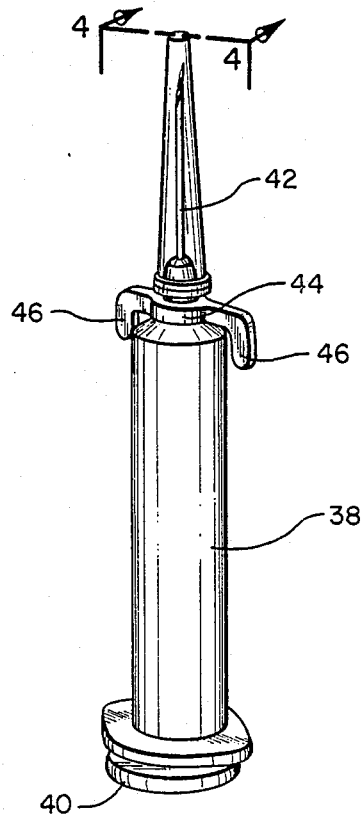
FIG. 3 is a side perspective view of an additional embodiment of the present invention.

An additional embodiment of the present invention is illustrated in FIG. 3. The embodiment of the invention in FIG. 3 is particularly adapted to be applied when using threaded needles and syringes (such as Luer lock devices). Conventional Luer connections involve simply threading a needle onto the end of the needle socket. Thus, when removal of the needle is desired it is necessary to twist the needle off in order to disengage the needle. As with the embodiments of the device illustrated in FIGS. 1 and 2, the device in FIG. 3 is applied to a conventional syringe of the type having a threaded needle socket. FIG. 3 illustrates the syringe barrel 38, the plunger 40, and the needle 42 which includes a threaded base.

The device in FIG. 3 comprises a collar 44 which may be similar in configuration to the collar illustrated in FIGS. 1 and 2. Attached to the collar are a pair of outwardly protruding flanges 46. Flanges 46 allow the user to simply rotate the flanges, which in turn moves collar 44 forward on the needle socket. This movement causes the threaded needle 42 to turn and finally to become disengaged from the needle socket.

Figure 4:
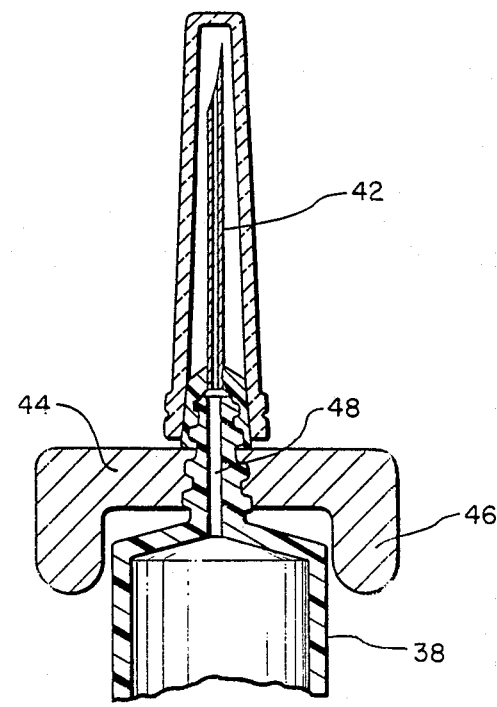
FIG. 4 is a cross-sectional view of the embodiment of the device illustrated in FIG. 3.

FIG. 4 illustrates in additional detail the embodiment of the device shown in FIG. 3. FIG. 4 is a cross-sectional view of the device illustrated in FIG. 3. From FIG. 4 it can be seen that the needle, the device, and the syringe barrel are in threaded engagement by means of the needle socket 48. As can be appreciated from FIG. 4, when the flanges 46 are rotated, the collar 44 is forced forward on the needle socket 48. This in turn causes the needle 42 to become disengaged from the end of needle socket 48.

Figure 5:
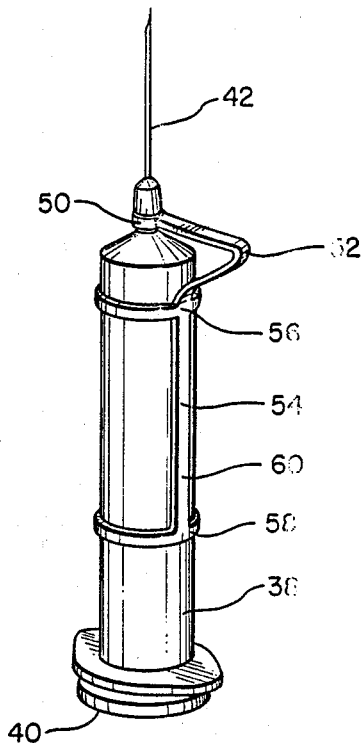
FIG. 5 is a side perspective view of an additional embodiment of the device.

FIG. 5 also illustrates an embodiment of the device for use in connection with needles having threaded bases. Again, a standard syringe barrel 38 having a threaded needle socket, plunger 40, and needle 42 are illustrated. The embodiment of the device illustrated in FIG. 5 comprises a collar 50 which is in turn connected to an outwardly extending curved arm 52. The outwardly extending curved arm 52 in turn is connected to a base structure 54. The base structure comprises a pair of rings 56 and 58 and a post 60 which connects the rings 56 and 60.

In operation, it is a simple manner to rotate the entire device, thus disengaging the threaded needle base from the syringe needle socket. The method of operation is similar to that described with respect to the embodiment of the device in FIGS. 3 and 4.

Figure 6:
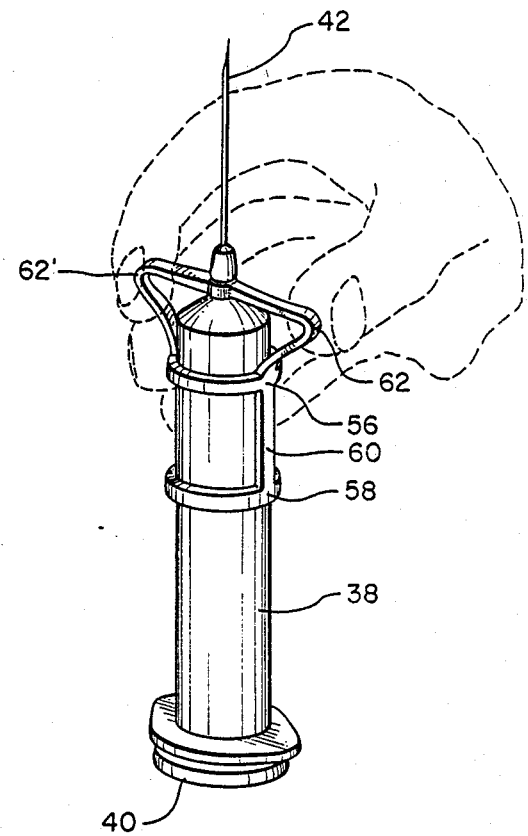
FIG. 6 is a side perspective view of an embodiment of the device similar to that in FIG. 5, except that it contains a pair of arms.

FIG. 6 illustrates an additional embodiment of the device similar to that illustrated in FIG. 5. The difference between the devices is that the embodiment in FIG. 6 comprises a pair of outwardly extending curved arms 62, rather than a single arm 52 as illustrated in FIG. 5.

Figure 7:
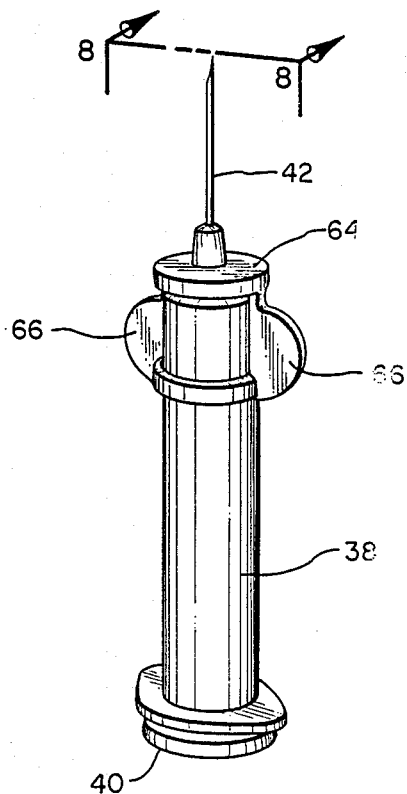
FIG. 7 is a side perspective view of an alternative embodiment of the present invention for use in connection with a Luer lock needle.
Figure 8:
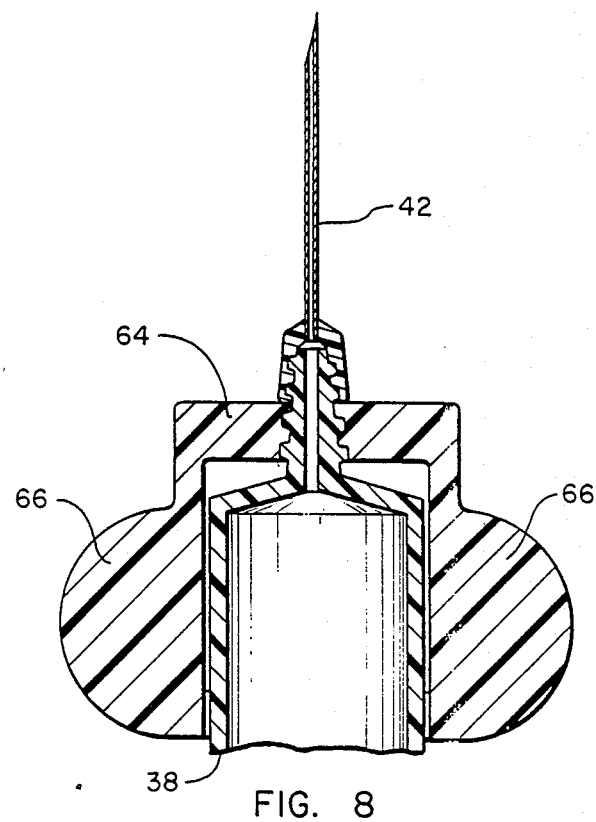
FIG. 8 is a cross-sectional view of the embodiment of the device illustrated in FIG. 7.

FIG. 7 illustrates an additional embodiment of the device related to threaded needles and needle sockets. This embodiment of the device also comprises a collar 64. The collar 64 is molded integrally with a pair of ears 66. The ears 66 form a type of wing nut structure. Thus, as illustrated in FIG. 8, twisting the ears 66 causes the collar 64 to move forward forcing the needle 42 from the end of the needle socket 48. Thus, it is possible to disengage the needle 42 from the syringe barrel 38 without the necessity of grasping the needle or any portion thereof.

In each of the embodiments of the device used on syringes comprising threaded needle sockets, it may be desirable to attach or anchor the collar to the base of the needle. In this manner, rotating the device and collar results in assured rotation of the needle. Thus, the needle can easily be disengaged from the needle socket.

Figure 9:
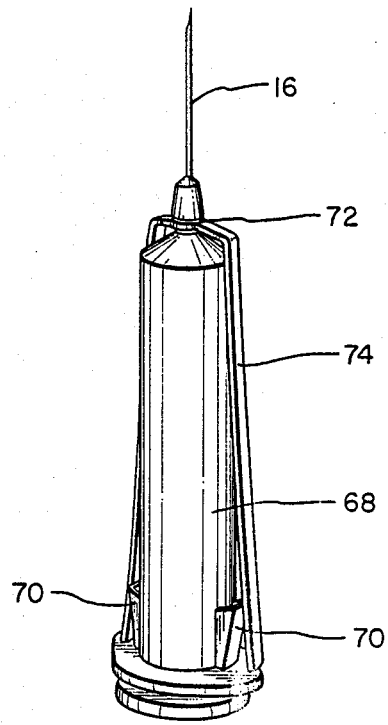
FIG. 9 is a side perspective view of an additional embodiment of the present invention.

The device illustrated in FIG. 9 comprises a collar 72 and a pair of arms 74. When using the syringe it may be desirable to simply leave the arms 74 disengaged from the sleeve 70. Thus, the arms 74 may be held tightly against the exterior of the syringe barrel 68 without causing the needle 16 to disengage.

Figure 9A:
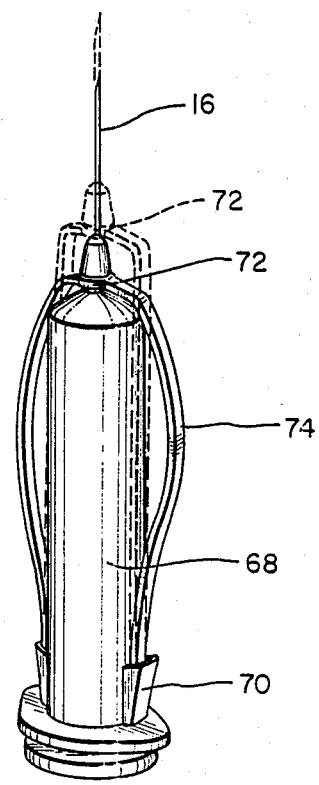
FIG. 9A is a side perspective view of the embodiment of the device illustrated in FIG. 9, illustrating the manner in which the arms fit within the sleeves.

When use of the needle 16 has been completed, the arms 74 are simply lifted outwardly and inserted into the sleeve 70 as illustrated in FIG. 9A. As further illustrated in FIG. 9A, when it is desired to disengage the needle 16 from the syringe barrel 68, the arms 74 are pressed inwardly while anchored in sleeves 70, moving the collar forward a sufficient distance to disengage the needle 16.

Figure 10:
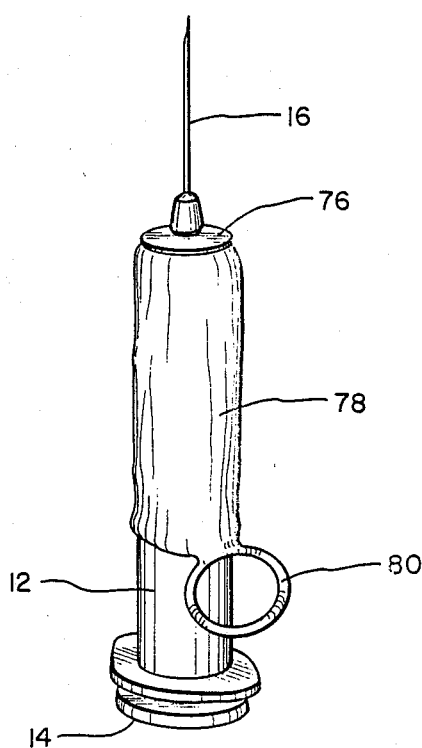
FIG. 10 is a side perspective view of an additional embodiment of the present invention.
Figure 10A:
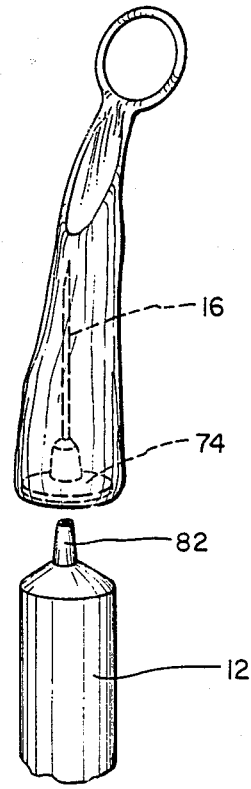
FIG. 10A is a side perspective view including phantom lines illustrating the manner of operation of the embodiment illustrated in FIG. 10.

An additional embodiment of the device is illustrated in FIGS. 10 and 10A. Again, a standard syringe barrel 12, plunger 14, and needle 16 are illustrated. This embodiment of the device comprises a collar 76. As with the other embodiments of the device, collar 76 is placed beneath the base of the needle 16 being disposed between the base of the needle 16 and the end of the syringe barrel 12. In this embodiment of the device, the collar 76 is secured to a flexible sheath 78. The sheath, in turn, may have a pull ring 80 attached to its base to allow for operation of the device.

When it is desired to remove the needle from the end of the syringe barrel 12, it is simply necessary to pull upwardly on the pull ring 80. This moves the flexible sheath upwardly and around the exterior of the needle 16. The sheath 78 will be sufficiently long to fully cover the needle 16. Thus, it is a simple matter to continue to move the sheath upwardly in the manner illustrated in FIG. 10A. This causes the needle 16 to disengage from the needle socket 82. Once the needle 16 is disengaged the entire sheath 78 together with the enclosed needle 16 may be disposed of without the necessity of grasping the needle 16.

It will be appreciated that the sheath 78 may be formed of any desirable material. Flexible plastics, rubber, and fabrics may all be used. It is only necessary for the sheath to be sufficiently flexible and durable to perform the desired function.

Figure 11:
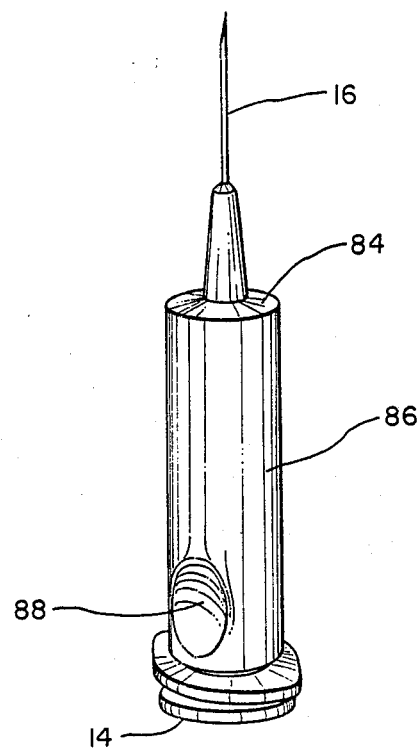
FIG. 11 is a side perspective view of an additional embodiment of the present invention.
Figure 11A:
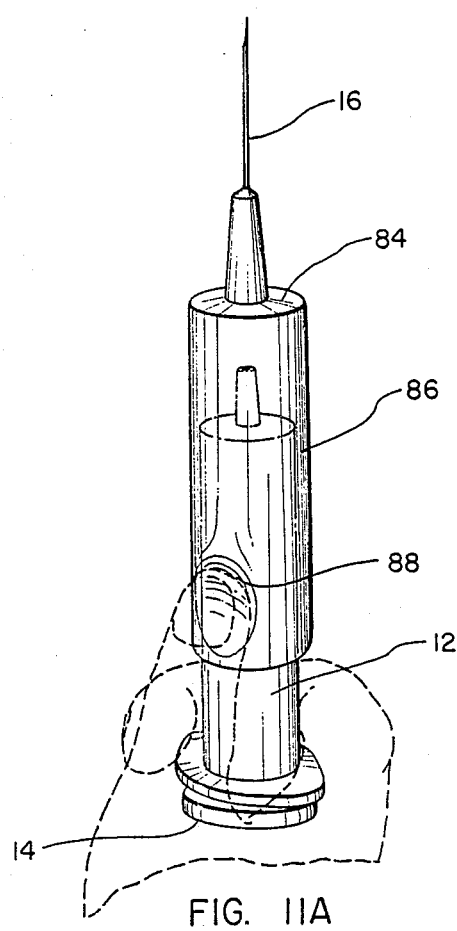
FIG. 11A is a side perspective view of the embodiment of the device illustrated in FIG. 11 showing the method of operation of the device.

A final embodiment of the present invention is illustrated in FIG. 11. As with the other embodiments of the invention, this embodiment is capable of fitting onto a standard syringe barrel 12. This particular embodiment of the present invention also includes a collar 84. The collar 84, as in the other embodiments of the device, fits between the base of the needle 16 and the end of the syringe barrel 12. Collar 84 is in turn securely attached to a rigid, generally cylindrical tube 86, which slides over the exterior of the syringe barrel 12. When it is desired to remove the needle from the ends of the syringe barrel 12, it is only necessary to move the rigid cylindrical tube 86 forward as is illustrated in FIG. 11A. This causes the collar 84 to move forward which in turn forces the needle 16 from the end of the needle socket.

As illustrated in FIG. 11, it may be desirable to place a thumb notch 88 on the proximal end of the tube 86.

This will allow the tube 86 to be more easily maneuvered forward when it is necessary to disengage the needle 16.

It will be appreciated that the various embodiments of the present invention can be formed of a variety of materials. For example, the embodiments that include the outwardly arms may preferably be formed of a flexible medical grade plastic material. Thus, it would be an easy matter to form a disposable device which is compatible with conventional and widely accepted disposable syringes. Alternatively, the device may be formed of metal, graphite, or other desirable material. It is only necessary that the material be sufficiently durable and flexible to perform the desired function.

With respect to the embodiments of the device for use in connection with a threaded needle, it may be desirable to form the device from a conventional metal or plastic material. Again, any material which has the mechanical characteristics necessary to perform the function is included within the scope of the present invention.

In summary, the present invention accomplishes all of the objects set forth above. The present invention provides methods and apparatus for safely removing used needles from the ends of hypodermic syringes. As discussed above, the removal of needles is a major cause of personal injury and accidents among hospital and medical personnel. Thus, the present invention provides a major safety feature at a reasonable cost. Furthermore, the present invention in several of its embodiments can be retrofit onto conventional and readily available syringes.

The present invention allows medical personnel to remove needles without the necessity of grasping the needle or the needle point. Simply grasping the device in the area of the syringe barrel is sufficient to force the needle forward such that it disengages from the needle socket. This is all accomplished by providing a collar device which resides between the base of the needle and the syringe body. The present invention provides various means for moving the collar forward in such a manner as to disengage the base of the needle. Thus, it will be appreciated that a major improvement in the art has been accomplished through the present invention.

It will be appreciated that the apparatus and methods of the present invention are capable of being incorporated in the form of a variety of embodiments, only a few of which have been illustrated and described above. The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed and desired to be secured by United States Letters Patent is:

1. An apparatus for removing needles from a hypodermic syringe, said syringe having a barrel having a needle socket at one end thereof such that a needle can be removably attached to said needle socket, the apparatus comprising:
    removal means disposed between a needle attached to the syringe and the syringe barrel; and
    means for causing said removal means to move generally away from the syringe barrel such that the needle becomes disengaged from the syringe socket, wherein said means for causing said removal means to move comprises at least one arm in communication with said removal means at its distal end and integrally molded to the syringe barrel at its proximal end, said at least one arm extending outwardly from the syringe barrel, such that when the outwardly extending portion of the arm is moved inwardly toward the syringe barrel, said removal means simultaneously moved forward a sufficient distance to disengage the needle from the needle socket, said arm being constructed such that when pressure on said arm is released it returns to its original configuration.

2. An apparatus for removing needles from a hypodermic syringe as defined in claim 1 comprising a pair of arms, said arms disposed on opposite sides of the syringe barrel.

3. An apparatus for removing needles from a hypodermic syringe as defined in claim 1 wherein said arms are formed from a flexible plastic material.

4. An apparatus for removing needles from a hypodermic syringe as defined in claim 1 wherein said arms are formed from a flexible metallic material.

5. An apparatus for removing needles from a hypodermic syringe as defined in claim 1 wherein said arms are formed of a flexible graphite material.

6. A device for disengaging needles from a syringe, said syringe having a barrel with a needle socket at one end thereof capable of receiving a hypodermic needle, the device comprising:
    a collar capable of being disposed between a needle attached to the needle socket and the syringe barrel;
    at least one flexible arm attached to the collar at its distal end and integrally molded to the syringe barrel at its proximal end, extending outwardly from the syringe barrel such that when the arm is moved inwardly toward the syringe barrel the collar moves forward a sufficient distance to disengage the needle from the syringe barrel.

7. A device for disengaging needles from a syringe as defined in claim 6 comprising two arms.

8. A device for disengaging needles from a syringe as defined in claim 6 comprising a plurality of arms.

9. An apparatus for removing hypodermic needles from hypodermic syringes as defined in claim 6 wherein said collar is generally disk shaped.

10. An apparatus for removing hypodermic needles from hypodermic syringes as defined in claim 6 wherein said collar comprises a hole through which said needle socket can protrude.

11. A hypodermic syringe comprising:
    a syringe barrel having a needle socket at one end thereof;
    a collar capable of being disposed between a needle attached to the needle socket and the syringe barrel; and
    means for causing the collar to move generally away from the syringe barrel such that the collar causes the needle to become disengaged from the syringe socket, said means for causing the collar to move comprising at least one arm attached to the collar at its distal end and attached to the syringe barrel at its proximal end, said arm being formed of a single piece of material and extending outwardly from the syringe barrel, such that when the outwardly extending portion of the arm is moved inwardly toward the syringe barrel, the collar is simultaneously moved forward a sufficient distance to disengage the needle from the needle socket, said arm being constructed such that when pressure on said arm is released it returns to its original configuration.

12. A hypodermic syringe as defined in claim 11 comprising a pair of arms, said arms disposed on opposite sides of the syringe barrel.

13. A hypodermic syringe as defined in claim 12 wherein said arms are permanently attached to the syringe barrel at their proximal ends.

14. A hypodermic syringe as defined in claim 11 wherein said arms are formed from a flexible plastic material.

15. A hypodermic syringe as defined in claim 11 wherein said arms are formed from a flexible metallic material.

16. A hypodermic syringe as defined in claim 11 wherein said arms are formed of a flexible graphite material.

* * * * *